US006251955B1

(12) United States Patent
Bulawa

(10) Patent No.: US 6,251,955 B1
(45) Date of Patent: Jun. 26, 2001

(54) METHODS FOR IDENTIFYING INHIBITORS OF FUNGAL PATHOGENICITY

(75) Inventor: Christine E. Bulawa, Arlington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/191,240

(22) Filed: Nov. 13, 1998

Related U.S. Application Data

(60) Continuation of application No. 08/823,347, filed on Mar. 24, 1997, now abandoned, which is a division of application No. 08/202,990, filed on Feb. 28, 1994, now Pat. No. 5,614,377.

(51) Int. Cl.$^7$ .............................. A61K 45/00; C12Q 1/02
(52) U.S. Cl. .............................. 514/789; 435/32; 514/19; 514/50; 424/600
(58) Field of Search .............................. 514/789, 19, 50; 424/600; 435/32

(56) References Cited

U.S. PATENT DOCUMENTS

| | | |
|---|---|---|
| 3,805,117 | 4/1974 | Hausman . |
| 4,242,720 | 12/1980 | Moore . |
| 4,246,595 | 1/1981 | Noyori et al. . |
| 4,628,406 | 12/1986 | Smith et al. . |
| 4,924,353 | 5/1990 | Patraw . |
| 4,981,817 | 1/1991 | Stone, Jr. . |
| 5,091,375 | 2/1992 | Hector et al. .......................... 514/50 |
| 5,149,795 | 9/1992 | Hector et al. .......................... 536/23 |
| 5,322,446 | 6/1994 | Cearley-Cabbiness et al. . |
| 5,451,165 | 9/1995 | Cearley-Cabbiness et al. . |
| 5,517,036 | 5/1996 | Semba et al. . |
| 5,614,377 | 3/1997 | Bulawa .................................. 435/32 |

FOREIGN PATENT DOCUMENTS

| | | |
|---|---|---|
| 42 04 459 A1 | 8/1993 | (DE) . |
| 42 32 404 A1 | 3/1994 | (DE) . |
| 195 07 547 C2 | 9/1996 | (DE) . |
| 427 328 A2 | 5/1991 | (EP) . |
| 465 195 A2 | 1/1992 | (EP) . |
| 554 622 A2 | 8/1993 | (EP) . |
| 673 193 A1 | 9/1995 | (EP) . |
| 2 153 144 | 8/1985 | (GB) . |
| 63-65632 | of 1988 | (JP) . |
| WO 89/02744 | 4/1989 | (WO) . |
| WO 95/23235 | 8/1995 | (WO) . |

OTHER PUBLICATIONS

Bulawa, C.E., "Genetics and Molecular Biology of Chitin Synthesis in Fungi," *Ann. Rev. Microbiol.*, 47:505–34 (1993).

Sudoh, M. et al., "Cloning of the Chitin Synthase 3 gene from *Candida albicans* and its Expression During Yeast–Hyphal Transition," *Mol. Gen. Genet.*, 241:351–358 (1993).

Bulawa, C.E., "CSD2, CSD3, and CSD4, Genese Required for Chitin Synthesis in *Saccharomyces cerevisiae*: the CSD2 Gene Product is Related to Chitin Synthasases and to Developmentally Regulated Proteins in Rhizobium Species and *Xenopus laevis*, " *Molecular and Cellular Biology* 12(4):1764–1776 (Apr. 1992).

Takita, M.A. and Castilho–Valavicius, B.,"Absence of Cell Wall Chitin in *Saccharomyces cerevisiae* Leads to Resistance to *Kluyveromyces lactis* Killer Toxin," *Yeast* 9:589–598 (1993).

Shaw, J.A. et al., "The Function of Chitin Synthases 2 and 3 in the *Saccharomyces cerevisiae* Cell Cycle," *The Journal of Cell Biology* 114(1):111–123 (Jul. 1991).

Chapman, T. et al., "Chitin Biosynthesis in *Candida albicans* Grown In Vitro and In Vivo and Its Inhibition by Nikkomycin Z," *Antimicrobial Agents and Chemotherapy* 36(9) :1909–1914 (Sep. 1992).

Silverman, S.J. et al., "Chitin Synthase 2 is Essential for Septum Formation and Cell Division in *Saccharomyces Cerevisiae,*" *Proc. Natl. Acad. Sci. USA*, 85:4735–4739 (Jul. 1988).

Cohen, E., "Chitin Synthesis and Degradation as Targets for Pesticide Action," *Archives of Insect Biochemistry and Physiology* 22(1–2):245–261 (1993).

Adams, D.J. and Gooday, G.W., "Chitin Synthesis as a Target–Current Progress," in *Systemische Fungizide und Antifungale Verbindungen*, pp. 39–45 (1983).

Bowen, A.R. et al., "Classification of Fungal Chitin Synthases," *Proc. Natl. Acad. Sci. USA*, 89:519–523 (Jan. 1992).

Valdivieso, M.H. et al., "CAL1 A Gene Required for Activity of Chitin Synthase 3 in *Saccharomyces Cerevisiae,*" *The Journal of Cell Biology*, 114(1):101–109 (Jul. 1991).

Bulawa, C.E. and Osmond, B.C., "Chitin synthase I and chitin synthase II are not required for chitin synthesis in vivo in *Saccharomyces cerevisiae,*"*Proc. Natl. Acad. Sci. USA* 87:7424–7428 (Oct. 1990).

Cabib, E., "Differential inhibition of chitin synthetases 1 and 2 from *Saccharomyces cerevisiae* by polyoxin D and nikkomycins," *Antimicrob. Agents Chemother* 35(1):170–3 (Jan. 1991).

(List continued on next page.)

*Primary Examiner*—Rebecca E. Prouty
(74) *Attorney, Agent, or Firm*—Hamilton, Brook, Smith & Reynolds, P.C.

(57) ABSTRACT

Methods of detecting inhibitors of fungal pathgenicity are disclosed. These methods are based on the discovery that pathogenicity is diminished when chitin synthase III is inhibited. The inhibitors of fungal pathogenicity are detected with mutant strains of *S. cerevisiae* or other mutant fungal strains, whose mutation causes diminished growth of the fungus when combined with the inhibition of chitin synthase III.

7 Claims, 3 Drawing Sheets

OTHER PUBLICATIONS

Bulawa, C.E. et al., "The *S. cerevisiae* structural gene for chitin synthase is not required for chitin systhesis in vivo," *Cell* 46(2):213–25 (Jul. 1986).

Khardori, N. et al., "Comparative efficacies of cilofungin (LY121019) and amphotericin B against disseminated *Candida albicans* infection in normal and granulocytopenic mice", *Antimicrob Agents Chemother*, 37(4) 729–36 (Apr. 1993).

Orlean, P., "Two Chitin Synthases in *Saccharomyces cerevisiae*", *The Journal of Biological Chemistry*, 262(12):5732–2739 (Apr. 1987).

McCarthy, P.J., et al., "Mechanism of Action of Nikkomycin and the Peptide Transport System of *Candida albicans*", *Journal of General Microbiology*, 131:775–780 (1985).

Hector, R.F. and Braun, P.C., "A 96–Well Epifluorescence Assay for Rapid Assessment of Compounds Inhibitory to Candida spp.", *Journal of Clinical Microbiology*, 24(4):620–624 (Oct. 1986).

Hector, R.F. and Schaller, K., "Positive Interaction of Nikkomycins and Azoles against *Candida albicans* In Vitro and In Vivo", *Antimicrobial Agents and Chemotherapy*, 36(6):1284–1289 (Jun. 1992).

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (xi) SEQUENCE DESCRIPTION: SEQ ID NO:1:

CCCAGGCCTC ACACAGATCA TTCGC      25

(2) INFORMATION FOR SEQ ID NO:2:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (xi) SEQUENCE DESCRIPTION: SEQ ID NO:2:

GTGAATCACG CTTACCTC      18

(2) INFORMATION FOR SEQ ID NO:3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:3:

CGATGAAACT GTGCCACCAG      20

(2) INFORMATION FOR SEQ ID NO:4:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (xi) SEQUENCE DESCRIPTION: SEQ ID NO:4:

CCCTCTAGAG GGACCCTTGA GTATTAGC      28

METHODS FOR IDENTIFYING INHIBITORS OF FUNGAL PATHOGENICITY

RELATED APPLICATIONS

This application is a continuation of U.S. Ser. No. 08/823,347, filed Mar. 24, 1997 now abandoned, which is a division of U.S. Ser. No. 08/202,990, filed Feb. 28, 1994, now issued as U.S. Pat. No. 5,614,377. The entire teachings of both of the referenced applications are incorporated herein by reference.

BACKGROUND OF THE INVENTION

Fungi are ubiquitous pathogenic organisms which can cause opportunistic infections in humans and other mammals. Some of these infections, although generally not life threatening, are widespread among the general population, occurring in one of the more common examples. In recent years, there has been an increase in infections caused by Candida and other fungal pathogens, especially those which have serious and even life threatening health implications. Such infections generally occur in patients with compromised immune systems, such as patients undergoing chemotherapy or corticosteroid treatments. This recent rise in life threatening fungal infections is largely a result of an increase in the number of transplants and the accompanying immunosuppressive therapies and of the spread of AIDS.

Unfortunately, there are few drugs available today for the treatment of fungal infections. Those that are available have serious shortcomings. They have a limited spectrum of activity, and many are toxic or are no longer effective because the target organism has become resistant. For example, pulmonary and disseminated infections caused by Aspergillus fumigatus in neutropenic or immunosuppressed patients are often fatal because treatments, such as the administration of Amphotericin B, are ineffective. Amphotericin B is also used for infections caused by Candida species, Cryptococcus neoformans, Blastomyces dermatidis, Coccodioides immitis, and Histoplasma capsultatum and has many undesirable side effects. Azoles, a class of anti-fungal agents (e.g. Fluconazole, used against Candida and Cryptococcus nerformans infections) can be effective, but are active against a limited range of fungi and resistant strains have emerged. Pneumocystis carinii is responsible for the most common opportunistic infection (pneumocystis pneumonia) in AIDS patients, in whom the infection is often fatal. Treatment with drugs such as trimethoprim-sulfamethoxazole and dapsone is often ineffective and may be limited by the drugs' toxicity.

Consequently, there exists a need for developing new therapies for treating infections by fungal pathogens. As an aid in developing new therapies, it would be of great value to have an assay which could rapidly detect new compounds which can interrupt a cellular process essential for growth or virulence of the fungi, and, thus, act as antifungal agents.

SUMMARY OF THE INVENTION

The present invention relates to a method of identifying inhibitors of fungal pathogenicity. These inhibitors may be fungistatic or fungicidal. This assay is based on the discovery that fungal pathogenicity is dependent on the levels of chitin in the cell wall and that pathogenicity can therefore be reduced or removed through the inhibition of chitin synthase III. In one embodiment of the method of the present invention, a mutant strain of fungus containing a mutated chitin synthase II gene is cultured in the presence of a molecule or compound to be assessed for its ability to inhibit chitin synthase III. If the molecule or compound is a chitin synthase III inhibitor, the mutant strain will show diminished growth when compared to the growth of wild type strain of fungus cultured under the same conditions in the presence of the molecule or compound. In a second embodiment of the present method, a first strain and a second strain of a fungus are cultured in the presence of a compound or molecule to be assessed for its activity as a chitin synthase III inhibitor. The first strain contains an inhibited chitin synthase II and shows diminished growth in the presence of a chitin synthase III inhibitor, compared to the growth of the second strain of fungus, which does not contain inhibited chitin synthase II, cultured under the same conditions in the presence of the molecule or compound.

DETAILED DESCRIPTION OF THE INVENTION

Figure 1:
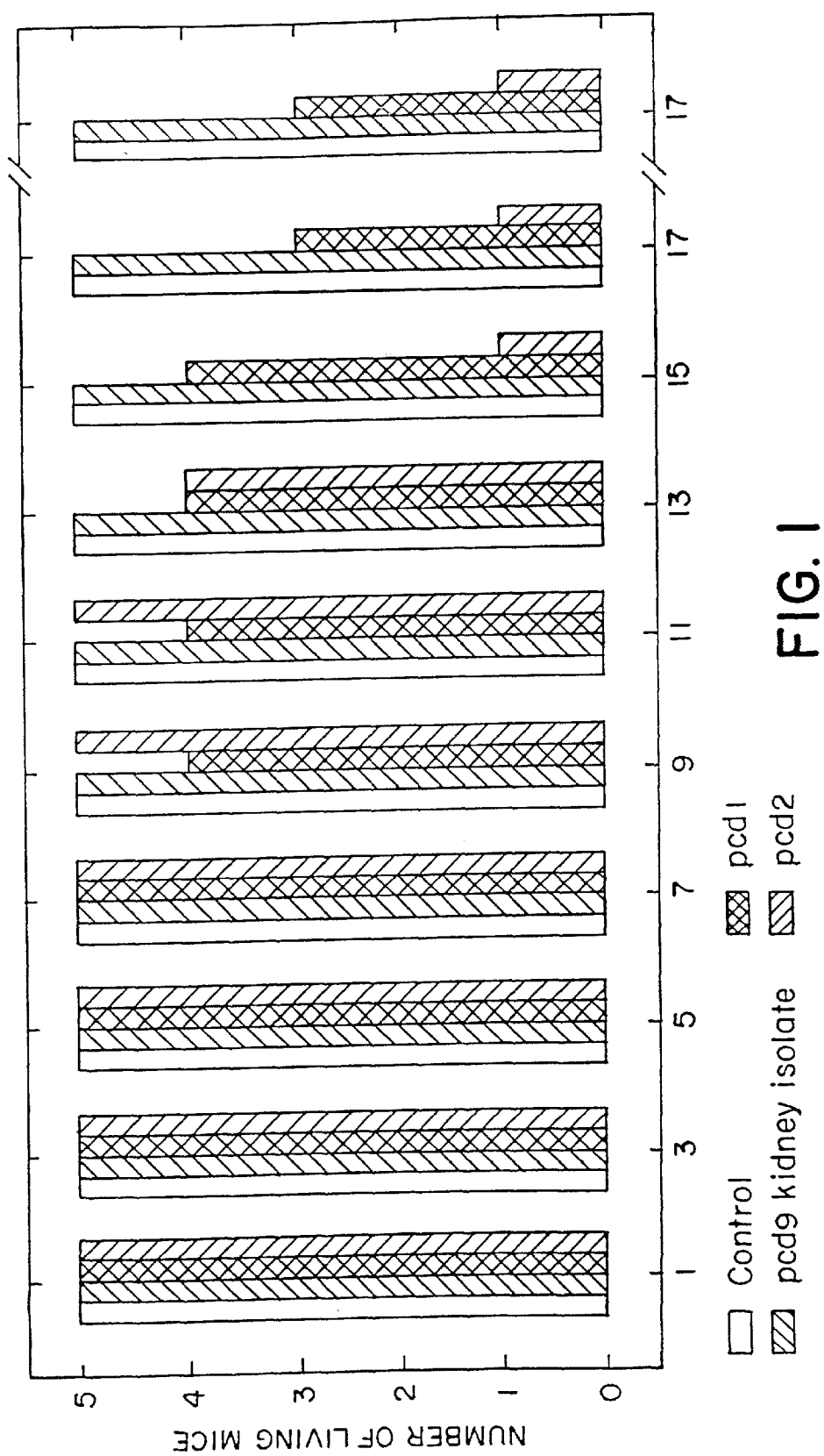
FIGS. 1 and 2 are graphical representations of the virulence of a wild type and mutant strains of Candida albicans ATCC 10261 against male ICR mnice.
Figure 2:
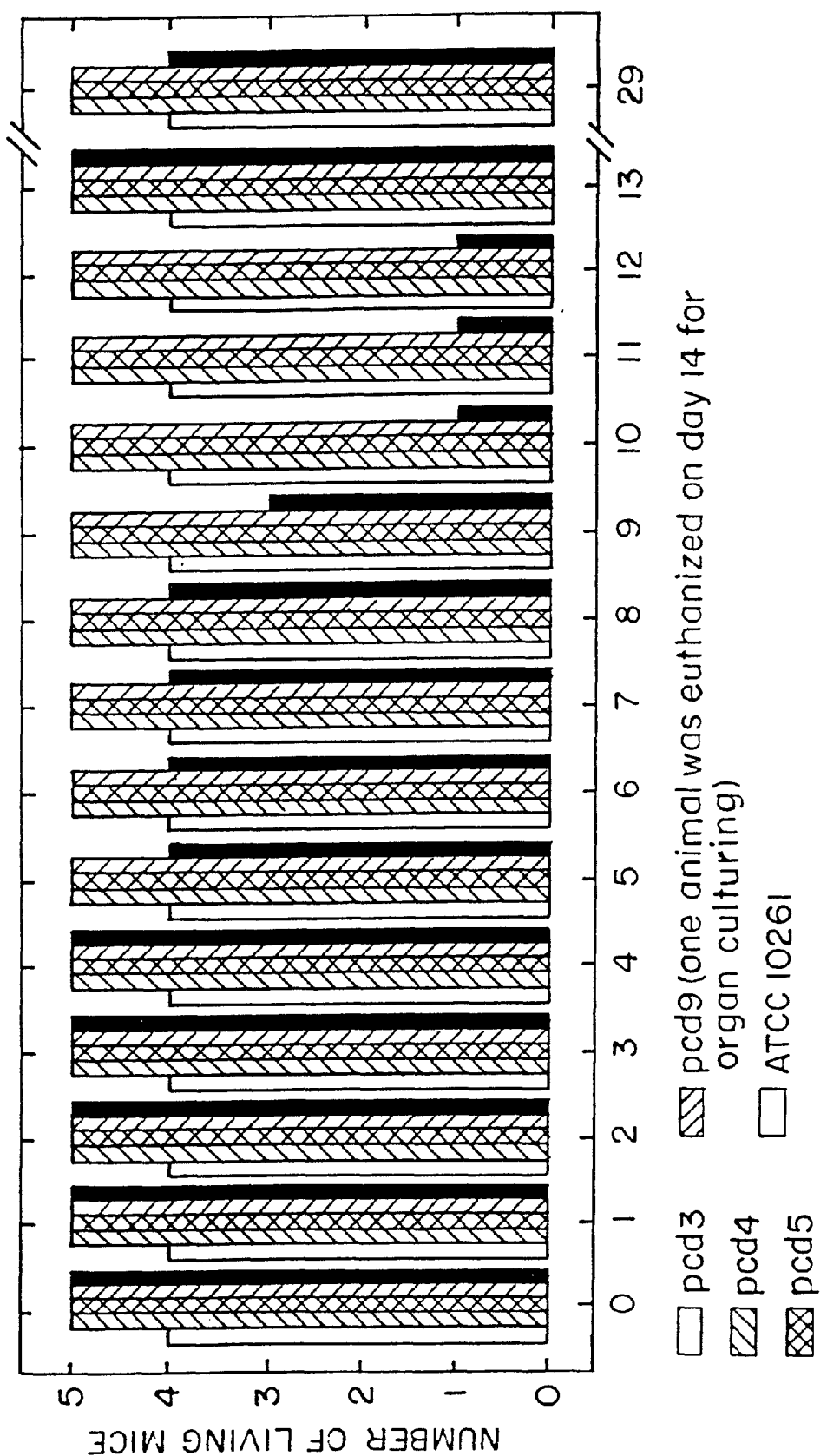
Figure 3:
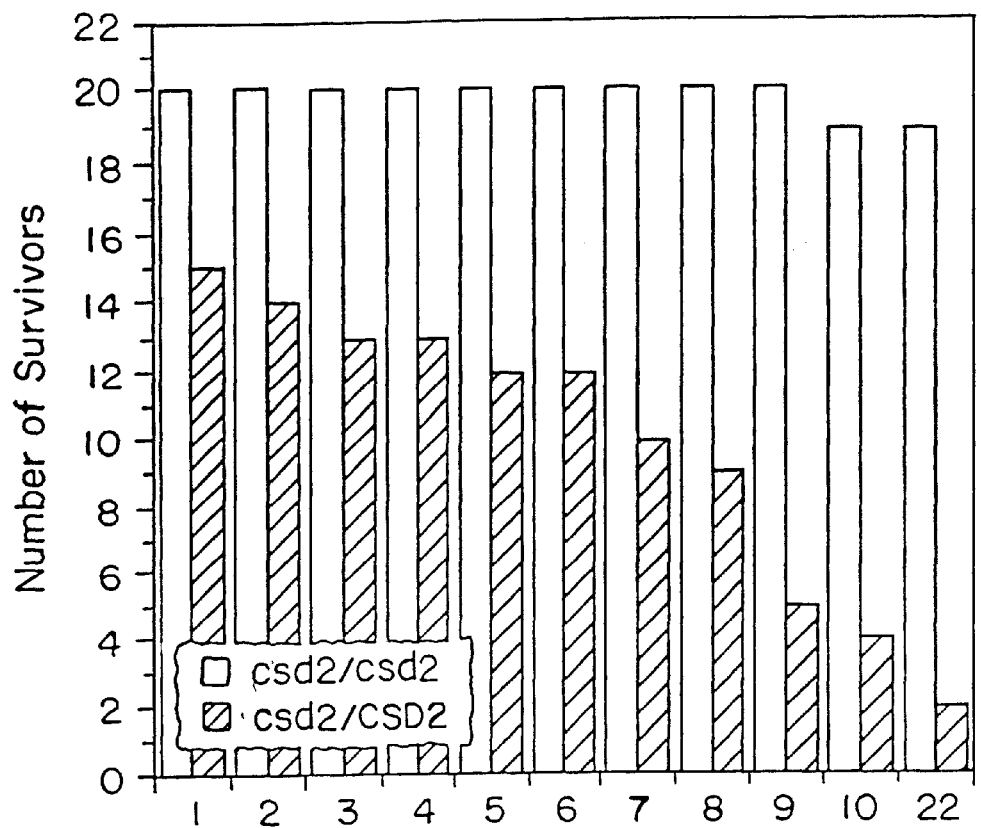
FIG. 3 is a graphical representation of the virulence of csd2/csd2 and csd2/CSD2 mutant strains Candida albicans against male ICR mice.

The present invention is based on the discovery that the pathogenicity of Candida albicans is dependent on the levels of chitin in the cell wall. Mutant strains of C. albicans that have substantial reductions (4- to 5-fold) in the amount of chitin in the cell walls have been shown to be up to ten times less virulent than wild type strain (see FIGS. 1–3 ). The present invention is an assay for detecting molecules and compounds which inhibit the production of chitin in fungi and, thus, provides an effective screen for compounds which diminish the pathogenicity of fungi and are effective treatments for fungal infections. The inhibitors identified by this assay may be fungistatic or fungicidal.

Chitin is a $\beta(1,4)$-linked polymer of N-acetylglucosamine that is an important constituent of the fungal cell wall. In Saccharomyces cerevisiae there are at least three enzymes that synthesize chitin: chitin synthase I, II and III. Chitin synthase I and chitin synthase II are encoded by the CHS1 and CHS2 genes, respectively. These enzymes make less than 10% of the cell wall chitin. Chitin synthase III accounts for the remaining 90% of cell wall chitin. Bulawa, Mol. Cell. Biol., 12:1764 (1992), Valdivieso et. al., J. Cell. Biol., 114:101 (1991) and Roncero et al, J. Bacteriol. 170:1950 (1988). C. albicans also contains CHS1 and CHS2 genes, which are closely related to the S. cerevisiae CHS genes (Au-Young and Robbins, Mol. Microbiol., 4:197 (1990), Bowen et al., Proc. Nat. Acad. Sci. U.S.A., 89:519 (1992), and Chen-Wu and Zwicker Mol. Microbiol., 12:1764 (1992)).

In S. cerevisiae chitin synthase III activity is dependent on three genes, CSD2, CSD4 and CAL3. In addition, one further gene, CSD3, encodes a product which is involved in chitin synthesis. Mutants defective in any of these genes show a ten-fold reduction in chitin synthesis (Bulawa, Annu. Rev. Microbiol., 47:505 (1993). Bulawa (1992) and Roncero et al. (1988) A homolog of CSD2 has been detected in C. albicans (Sudoh et al. Mol. Gen. Genet. 241:351 (1993)). Disruption of this gene (Examples 1 and 2) causes a five-fold reduction in chitin synthesis.

The present invention relates to a method of detecting compounds which cause diminished pathogenicity of pathogenic fungi by decreasing cell wall chitin content by inhibiting cellular components which participate in chitin synthesis, such as chitin synthase III.

One embodiment of the present invention relates to a method of identifying an inhibitor of fungal pathogenicity by assessing the effects of a compound on a mutant strain of fungus which contains a mutated gene which results in diminshed growth of the mutant fungus when chitin synthase III is also inhibited. Inhibition of chitin synthase III refers to the selective prevention, reduction or diminution in function of one or all of the proteins which make up the chitin synthase III enzyme complex. It also refers to the selective prevention, reduction or diminution in expression of the protein product encoded by the chitin synthase gene(s). Inhibition of chitin synthase III also refers to selective prevention of the transport or incorporation of chitin into the fungal cell wall. When used in reference to chitin synthase III, the term "selective" or "selectivity" means that the result (e.g., inhibition, prevention, reduction) is specific in that it affects predomninantly chitin synthase III or chitin synthase II and III.

Inhibitors of fungal pathogenicity can be identified by culturing the mutant strain of fungus in the presence of the suspected inhibitor under conditions appropriate for the growth of the mutant strain. Examples of such conditions are given in Examples 5 and 6. The skilled artisan will recognize many other conditions which are suitable for growth of the mutant and wild type strains of fungus and can be used in this assay. The wild type strain of fungus must be cultured in the presence of the suspected inhibitor (test molecule or compound) under the same conditions as the mutant strain. The growth of the mutant strain is then compared to the growth of the wild type strain. Compounds that diminish the growth of the mutant strain, but do not inhibit the growth of the wild-type strain, are specific inhibitors of chitin synthase III and putative inhibitors of pathogenicity. Compounds that diminish the growth of the mutant strain more than the growth of the wild-type strain are preferential inhibitors of chitin synthase III and putative fungistatic or fungicidal agents. Compounds that equally diminish the growth of the mutant strain and the wild-type strain act by a mechanism other than inhibition of chitin synthase III and may be toxic agents.

One example of such a mutant strain of fungus is one in which the CHS2 gene is mutated. This example is based on the discovery that mutations of CHS2, CSD2, CSD4 or CAL3 are not, by themselves, lethal but that mutations in CHS2 in combination with the inhibition of chitin synthase III, as defined hereinabove, are growth inhibiting. The combination of a CHS2 mutation with chitin synthase III inhibition and its lethal effect has been observed in a mutated strain of *Saccharomyces cerevisiae* containing a disrupted CHS2 gene (Shaw et al. *Mol. Cell Biol.* 114:111 (1991). The procedures for creating this mutant strain and data demonstrating the growth inhibiting effect of this combination are described more fully in Examples 4 and 5.

A second example of such a mutant strain is one in which the ssd1 gene has been mutated such that its protein product is defective. A defective ssd1 protein gene product is one whose function has been selectively reduced, diminished or eliminated. This defective ssd1 protein gene product is also one whose expression has been selectively reduced, diminished or eliminated. When used in reference to SSD1, the term "selective" or "selectivity" means that the result (e.g., reduced, diminished or eliminated) is highly specific in that it affects predominantly SSD1.

The SSD1 gene product is thought to play a role in protein phosphorylation. Although mutants defective in ssd1 show no obvious phenotype, ssd1 csd2 double mutants are temperature sensitive for growth. The growth sensitivity of the ssd1 csd2 double mutants occurs at temperatures from about 35° C. to about 39° C. on media of low osmolarity (conditions of low osmolarity are defined in Bulawa, *Mol. Cell. Biol.*, 12:1764 (1992) on pages 1767–8 in the section "The temperature sensitivity of csd2, csd3 and csd4 can be suppressed"). (Bulawa *Mol. Cell. Biol.*, 12 :1764 (1992), Bulawa *Ann. Rev. of Microbiol.*, 47:505 (1993)). A preferred temperature for growing these ssd1 mutants is 37° C. on media of low osmolarity. Procedures for creating this mutant and for performing the assay for detecting chitin synthase III inhibitors are described more fully in Example 6.

In a second embodiment of the assay of the present invention, an inhibitor of fungal pathogenicity is identified through the use of a first fungal strain and a second fungal strain. The first fungal strain contains inhibited chitin synthase II, which refers to the selective prevention, reduction or diminution in function of one or all of the proteins which make up chitin synthase II. It also refers to the selective prevention, reduction or diminution in expression of the protein product of the genes which encode chitin synthase II. Inhibited chitin synthase II is the result of alteration of chitin synthase II DNA in such a manner that the encoded protein is defective (non-functional) or is not expressed or is the result of interference with the function of the expressed synthase (e.g., by preventing it from participating in chitin synthesis). The second fungal strain does not contain inhibited chitin synthase II.

In this embodiment, an inhibitor of fungal pathogenicity is identified by growing both fungal strains in the presence of a suspected inhibitor under conditions appropriate for the growth of the fungus. Examples of such conditions are given in Examples 5 and 6. The skilled artisan will recognize many other conditions which are suitable for growth of these strains of fungus and can be used in this assay. The growth of the first strain is then compared to the growth of the second strain. Diminished growth of the first strain, compared to growth of the second strain, is indicative of the inhibition of chitin synthase III. Diminished growth in both strains is indicative of the toxicity of the test molecule or compound to the fungus.

Another embodiment of the present invention relates to a method of identifying an inhibitor of fungal pathogenicity by assaying for inhibitors of chitin synthase III by use of isolated chitin synthase III. In this method, a first sample of isolated chitin synthase III is contacted, under conditions suitable for chitin synthase III activity, with a compound or molecule to be assessed for its ability to inhibit chitin synthase III and a chitin synthase III substrate, thereby producing a test sample. Suitable conditions include appropriate pH and metal ion concentrations, which can be readily determined by those skilled in the art. A second sample of the isolated chitin synthase III is combined with a chitin synthase III substrate to produce a control sample. The control is maintained under the same conditions as the test sample. The test sample and the control sample are then assessed for the amount of chitin produced. The presence of an inhibitor of chitin synthase is indicated when less chitin is produced by the test sample relative to the amount produced by the control sample.

Isolated chitin synthase III refers to chitin synthase III which has been obtained by disruption of cells (i.e., it is a component of a preparation which contains other substances, such as membranes) or which is substantially free of other substances. The isolated enzyme can be obtained by biochemical isolation procedures known to those skilled in the art. Alternatively, isolated chitin synthase III can be obtained by molecular cloning techniques. For example, the *C. albicans* CSD2 gene has been cloned and sequenced by Sudoh et al., *Mol. Gen. Genet.*, 241:351 (1993) (CSD2 is referred to in this reference as CACHS3). This gene can be introduced into an appropriate vector, which can in turn be introduced into a host appropriate for the expression of the transfected gene. The techniques for carrying out these operations as well as techniques for isolating the protein gene product are known to those skilled in the art.

Methods for assaying the amount of chitin produced by a sample of isolated chitin synthase III are known in the art. For example, preparations containing isolated chitin synthase III can be incubated with labeled substrate, for example, UDP-[U—$^{14}$C]-N-acetylglucosamine, under conditions that permit chitin synthesis, such as 1 mM UDP-[U—$^{4}$C]-N-acetylglucosamine, 40 mM N-acetylglucosamine, 50 mM Tris-HCl, pH 7.5, and 5 mM $MgCl_2$ at 25° C. Unreacted substrate can be removed, for example, by filtration, centrifugation, or chromatography and the amount of product quantitated.

Another embodiment of the present invention relates to methods of identifying inhibitors of fungal pathogenicity by assaying for inhiitors of chitin synthase III in cells or spheroplasts. Because it makes 90% of the chitin in cells, chitin synthase III can be assayed by measuring the amount of chitin made by living cells. In this method, a first set of fungal cells, for example *S. cerevisiae*, or spheroplasts is incubated under conditions appropriate for their growth. The incubation is carried out in the presence of a molecule or compound to be assessed for its ability to reduce chitin production. This first set of cells or spheroplasts is referred to as the test set. A second set of fungal cells or spheroplasts, referred to as a control set, is incubated under conditions appropriate for their growth. After a suitable period of time, the amount of chitin produced by each set is then determined. An inhibitor of fungal pathogenicity is a compound or molecule that results in less chitin being produced in the test set than in the control set.

Methods of assaying for the amount of chitin produced by cells are known in the art. For example, cells can be incubated in the presence of a labeled precursor, such as $^{14}$C-glucosamine. The labeled chitin can be separated from other labeled cellular components such as mannan by treating with hot alkali; mannan is soluble while chitin is not.

A second procedure for measuring chitin synthase III activity is by assessing the synthesis of chitin by spheroplasts. Spheroplasts can be made by treating cells with hydrolytic enzymes that digest the cell wall, such as zymolyase, under conditions that prevent lysis, such as buffers containing 1 M sorbitol, or 0.6 M $MgCl_2$. The spheroplasts can be transferred to conditions that permit the resynthesis of the cell wall. The amount of chitin made during wall regeneration can be determined using labeled compounds that bind chitin, such as Calcofluor or FITC-labeled wheat germ agglutinin.

The compounds and molecules identified by the assays of the present invention as being chitin synthase III inhibitors can be further assayed for useful antifungal activity, as, for example in animal models such as rats, mice or rabbits by determining the ability of these compounds or molecules to control specific fungal infections. In addition, the biological activity of the identified compounds can be increased or optimized using techniques well known in the art. Increasing or optimizing the biological activity refers to modifying the chemical structure of an inhibitor identified by the present method in such a manner that the desirable physical and chemical properties of the compound are enhanced. For example, inhibitors can be modified in such a manner that their uptake into cells is enhanced, their resistance to degradation by cellular mechanisms is increased, their specificity and/or affinity is enhanced, their pharmacokinetics is improved and their distribution to infected tissues is improved. These properties can be assayed using the methods of the claimed invention, enzymatic assays, tests in animal models or other methods known in the art.

This method is useful for identifying inhibitors of all types of fungi, especially *Saccharomyces cerevisiae*, Candida species, *Aspergillus fumigatus, Cryptococcus neoformans, Pnueomocystis carinii, Blastomyces dermatitidis, Histoplasma capsulatum,* Trichophyton species, Microsporium species, *Coccidioides immitis* and plant pathogens such as *Rhizoctonia solani*, Alternaria species, Fusarium species, Pyricularia species and Puccinia species. Compounds or molecules identified in this way can be tested for their ability to inhibit another strain of fungus by contacting the compound or molecule with that strain of fungus. Alternatively, similar mutants can be created in other strains of fungi for use in assays in which methods similar to ones described herein are employed.

The molecules and compounds identified by the methods of the present invention as inhibitors of fungal pathogenicity can be used to treat individuals or plants infected with fungal pathogens. The individuals can be humans or non-human animals. Similarly, fungal contaminants can be removed from agricultural products by treating these products with the compounds and molecules identified by the methods of the present invention. The identified inhibitors can be administered, using known methods, by a variety of methods, including orally, rectally, vaginally, or by parenteral routes (e.g., intramuscular, intravenous, subcutaneous, nasal or topical). The form in which the inhibitors are administered will be determined by the route of administration. Such forms include, but are not limited to capsular and tablet formulations (for oral, vaginal and rectal administration), liquid formulations (for oral, intravenous, intramuscular or subcutaneous administration), slow releasing microcarriers (for rectal, intramuscular or intravenous administration), and creams or ointments (for topical administration). The formulations can also contain a physiologically acceptable vehicle and optional adjuvants, flavorings, colorants and preservatives. Suitable physiologically acceptable vehicles may include saline, sterile water, Ringer's solution, and isotonic sodium chloride solutions. The specific dosage level of active ingredient will depend upon a number of factors, including biological activity of the particular preparation and age, body weight, sex and general health of the individual being treated. These molecules and compounds can also be administered to infected individuals in combination with other known antifungal agents.

The molecules and compounds identified by the above assay can be co administered with other antifungal agents, to produce a combination of drugs which can act synergistically. The specific combination of agents will vary, depending on a number of factors, including activity of the agents, their side-effects, the particular infection(s), and the weight, age, sex and general health of the individual being treated.

Chitin is also an essential component of the exoskeleton of insects. A number of commercial insecticides, for example diflubeuzuron (see The Merck Index, Eleventh Edition, page 495, 1985), act by inhibiting chitin incorporation into cuticle. This demonstrates that chitin synthases and enzymes which assemble chitin are valid targets for new insecticides. Consequently, the assays of the present invention can also be used to identify new insecticides which act by inhibiting chitin synthase III or chitin synthase II and chitin synthase III. The method of identifying an insecticidally active compound or molecule comprises the steps of culturing a mutant fungal strain, which contains a mutated gene whose presence in the mutant fungal strain together with inhibited chitin synthase III results in inhibited growth of the mutant fungal strain. The mutant fungal strain is cultured in the presence of a molecule or compound to be assessed for insecticidal activity under conditions appropriate for growth of the mutant fungal strain. In addition, the corresponding wild type fungal strain is cultured under the same conditions as the mutant strain. The growth of the mutant fungal strain and the growth of the corresponding wild type fungal strain are compared. If growth of the mutant fungal strain is less than growth of the wild type fungal strain, the molecule or compound is insecticidally active. Compounds or molecules identified by this strain as being insecticidally active can be used to kill insects, for example for eradicating an insect infestation on plants or in an area such as a building.

The invention is further illustrated by the following examples, which are not intended to be limiting in any way.

DESCRIPTION OF CULTURE MEDIA

The medium used to grow the fungi in the subsequent Example 5 and Example 6 is minimal allantoin agar (MAA). This medium contains 0.17 g/L yeast nitrogen base without ammonium sulfate and amino acids (Difco Labs, Detroit, Mich.), 1 mg/ml allantoin, and 2% agar. For auxotrophic strains, the medium was supplemented with amino acids, adenine, and/or uracil at 30 µg/ml as required.

EXAMPLE 1

Creation of Chitin Deficient Mutants of C. albicans By Treatment with a Chemical Mutagen Mutants were isolated in the first procedure by treating a C. albicans strain ATCC10261 with 3% ethylmethanesulfonate at 30° C. in accordance with the method described for S. cerevisiae by Sherman et al., Meth. Yeast Genet, 11 (1986). Aliquots of washed cells were plated onto YPD agar (1% yeast extract, 2% peptone, 2% glucose) containing 0.1 mg/ml of Calcofluor. Resistant colonies were obtained after 3 to 4 days incubation at 30 ° C. at a frequency of 1 per 10,000 to 100,000 viable cells. For each of the mutants, cell wall chitin was evaluated. Cell wall chitin was measured as described in Bulawa et al., Cell, 46:213 (1986) with the exception that Serratia marcescens chitinase was replaced by Streptomyces plicatus chitinase and cytohelicase was replaced by β-glucuronidase (Sigma G-1512, approx. 600, 000 units/g, 2 mg/100 mg wet yeast cells). Both digestions were performed for 2 hours at 37 ° C. From a total of fourteen Calcofluor-resistant mutants, four were shown to be chitin-deficient, containing less than 20% of the amount of chitin present in a wild-type cell. The results are provided in Table I.

TABLE I

Amount of Chitin in Calcofluor-Resistant Mutants Obtained by EMS Mutagenesis

| Strain | µg chitin/mg cells | % of wild-type |
|---|---|---|
| ATCC 10261 | 1.73 | 100 |
| pcd2 | 1.35 | 71 |
| pcd3 | 0.36 | 19 |
| pcd4 | 0.33 | 17 |
| pcd5 | 0.34 | 18 |
| pcd9 | 0.23 | 12 |

EXAMPLE 2

Creation of Chitin Deficient Mutants of C. albicans by Disruption of CSD2

The C. albicans CSD2 gene (hereinafter "CaCSD2") is a homolog of S. cerevisiae CSD2. CaCSD2 has also been designated CHS3. The nucleotide sequence of CaCSD2 can be found in GenBank D13454. CaCSD2 was synthesized in two pieces from C. albicans chromosomal DNA using two pairs of oligonucleotide primers and the polymerase chain reaction. The first primer pair was synthesized from a first oligonucleotide (5'CCCAGGCCTCACACAGATCATTCGC; SEQ ID #1) and a second oligonucleotide (5'GTGAATCACGCTTACCTC; SEQ ID #2). In the formula for the first oligonucleotide, the CACACAGATCATTCGC nucleotides are nucleotides 27–43 of GenBank D13454. In addition, a StuI site was added at the 5' end of the first oligonucleotide to facilitate subsequent cloning. The second oligonucleotide, was the complement of the nucleotides 2648–2665 of GenBank D13454. Using polymerase chain reaction and the first primer pair, a 2.6 kb fragment was synthesized. The pairing reaction was carried out in a solution of 10 mM Tris-HC1, (pH 8.3), 50 mM KCl, 1.5 mM MgCl$_2$, 0.2 mM of each of dNTP, approx. 1 µM of each primer, 5–10 ng/µl SGY243 chromosomal DNA, and 0.05 unit/µl TAQ polymerase. After incubation at 92° C. for 3 minutes, the mixture was subjected to 31 amplification cycles, comprising 1 minute denaturation at 92° C., 30 seconds annealing at 62° C., and a 3 minute extension at 72° C., followed by a 7 minute incubation at 72° C.

The second primer pair was synthesized from a third oligonucleotide (5'CGATGAAACTGTGCCACCAG; SEQ ID #3), which was nucleotides 2547–2566 of GenBank D13454, and a fourth oligonucleotide (5'CCCTCTAGAGGGACCCTTGAGTATTAGC; SEQ ID #4) wherein the complement of nucleotides 4551–4570 of GenBank D13454 was GGGACCCTTGAGTATTAGC and an XbaI site was added at the 5' end to facilitate subsequent cloning. Using polymerase chain reaction and the second primer pair, a 2.0 kb fragment was synthesized. The polymerase chain reaction was the same as for the first primer pair except that the concentration of MgCl$_2$ was 6 mM.

The two fragments overlapped by 119 nucleotides. A single Asp718=KpnI site (the only one in GenBank D13454) was located in the overlap region, and the fragments were joined at this site to give the intact CaCSD2 gene. Standard molecular cloning protocols and reagents were used. The first fragment was digested with StuI and Asp718, while the second fragment was digested with XbaI and Asp7l8. These fragments were ligated into the HincII and XbaI sites of pSKΔEcoRIEcoRV, a derivative of pSK lacking the EcoRI and EcoRV sites in the polylinker, to give pCHC2-8.

To make a disrupted allele of CaCSD2 (csd2::hisG__URA3__hisG), 1.8 kb or approximately 50% of the open reading frame was replaced with the "URA blaster" cassette, which is a 4 kb molecular construct consisting of functional *C. albicans* URA3 gene flanked by direct repeats of a bacterial hisG gene (Fonzi and Irwin, *Genetics*, 134:717 (1993)). pCHC2-8 was digested with EcoRI, the ends were filled in with Klenow fragment, and BglII linkers, 5'd (pCAGATCTG), were added to yield pCHC2-9. The "URA blaster" cassette was inserted into this plasmid. To obtain the cassette, pMB-7 was cut with SalI, the ends were made blunt with Klenow, and then a second digestion was performed with BglII. The 4 kb fragment was ligated into the EcoRV and BglII sites of pCHC2-9 to give pCHC2-11.

The pCHC2-11 was digested with PstI and NotI to produce a 7 kb linear fragment containing the disrupted gene. Approximately 1 μg of this digest was used to transform CAI-4 (ura3::imm434/ura3::imm434). Uridine prototrophs were selected on solid synthetic medium (SD; 0.7% Difco yeast nitrogen base, 2% glucose, 2& agar). Several transformants were grown to saturation in medium (YPD) that contains uridine. In a small percentage of the cells, recombination occurred between the hisG repeats, deleting URA3 and one copy of hisG. The URA Cacsd2::hisG/CSD2 heterozygotes were recovered by plating a portion of each culture on medium containing 5-fluoroorotic acid prepared as described by Boche et al., *Mol. Gen. Genet.*, 197:354 (1984), except that uracil was replaced by uridine. The Cacsd2::hisG/CSD2 heterozygotes were subjected to a second round of transformation with the Cacsd2::hisG__URA3__hisG as described above.

Two types of transformants were obtained at high frequency; 1) Cacsd2::hisG__URA3__hisG/Cacsd2::hisG, due to integration of the disrupted gene at CSD2, and Cacsd2::hisG__URA3__hisG/CSD2, due to the integration of the disrupted gene at Cacsd2::hisG. To distinguish between themn, the transformants were scored for Calcofluor resistance on YPD agar containing 0.5 mg/ml Calcofluor. Cacsd2::hisG__URA3__hisG/Cacsd2::hisG is Calcofluor resistant and Cacsd2::hisG__URA3__hisG/CSD2 is Calcofluor sensitive. The genotypes were confirmed by Southern analysis as described by J. Sambrook et al., "*Molecular Cloning: A Laboratory Manual*", Second Edition, 9.31–9.58 (1989).

Disruption of CaCSD2 also produced a chitin deficient strain of *C. albicans*, as shown in Table II:

TABLE II

Amount of Chitin in Mutants Homozygous or Heterozygous for a Disrupted Allele of CaCSD2

| Strain | Relevant genotype | Chitin (μg/mg cells) |
|---|---|---|
| CACB3B-5 | csd2::hisG/csd2::hUh | 0.286 |
| CACB8B-5 | csd2::hisG/csd2::hUh | 0.305 |
| CACB10B-6 | csd2::hisG/csd2::hUh | 0.291 |
| CACB10B-10 | csd2::hisG/csd2::hUh | 0.316 |
| CACB3A | csd2::hisG/CSD2 | 1.34 |
| CACB8B-6 | csd2::hUhiCSD2 | 1.85 |
| CACB10B-8 | csd2::hUh/CSD2 | 1.80 |
| CAI-4 | CSD2/CSD2 | 1.98 |

Cell wall chitin was measured by the Bulawa method: (Bulawa et al. Cell 46:23 (1986).
Average, Csd2$^+$ = 1.74 μg/mg cells.
Average, Csd2$^-$ = 0.30 μg/mg cells or 17% of normal level.
The mutations in csd2 are deletion disruptions: csd2::hUh represents csd2::hisG__URA3__hisG.

The mutations in csd2 are deletion disruptions: csd2::hUh represents csd2::hisG__URA3__hisG.

The data in Table II demonstrate that the inhibition of Chitin Synthase III results in an 80–90% decrease in the synthesis of cellular chitin. Any compound that causes a similar decrease is therefore an inhibitor of Chitin Synthase III. Nikkomycin Z has been shown to strongly iniibit the production of cellular chitin in *C. albicans* (T. Chapman et al, *Antimicrobiol. Agent Chemother.*, 36:1909 (1992)). It can therefore be concluded that Nikkomycin Z inhibits this enzyme.

EXAMPLE 3

Virulence of the Chitin Deficient Mutants

The virulence of chitin-deficient mutants of *C. albicans* ATCC 10261 strains was tested against male ICR mice. The mice were obtained from the Harlan Sprague-Dawley Co., Indianapolis, Ind. Male ICR mice, weighing between 20–25 grams, were infected by tail vein injection with $10^6$ CFU of the *C. albicans* strains on day zero. Mortality and morbidity were monitored twice daily for a period of 29 days post-infection. Moribund mice were euthanized by cervical dislocation. Kidneys and spleens were removed after death to verify colonization by *C albicans*. The virulence study results for mutants of *C. albicans* ATCC 10261 are provided in FIGS. 1 and 2.

The virulence of chitin-deficient csd2/csd2 and csd2/CSD2 *C. albicans* mutant strains was tested against male ICR mice. Male ICR mice, weighing between 20–25 grams, were infected with $10^6$ CFU of the *C. albicans* strains on day zero in accordance with the method described in F. C. Odds, *Candida and Candidosis* 2nd Ed., W. B. Saunders, London 280 (1988) and N. Khadori et al., *Antimicrobiol. Agent Chemother.*, 37:729 (1993). Mortality and morbidity were monitored twice daily for a period of 29 days post-infection. Moribund mice were euthanized by cervical dislocation. Kidneys and spleens were removed after death to verify colonization by *C. albicans*. The virulence study results for csd2/csd2 and csd2/CSD2 *C. albicans* strains are provided in FIG. 3.

EXAMPLE 4

Creation of a *S. cerevisiae* CHS2 Deficient Mutant

Standard molecular biology techniques were used to disrupt *S. cerevisiae* CHS2 (Genbanak M23865). The construction was performed as described in Silverman et al. *Proc. Natl. Acad. Sci. USA*, 85:4735 (1988), except that TRP1 was used as the selectable marker instead of LEU2. Plasmid pSS2 (Silverman et al. *Proc. Natl. Acad. Sci. USA*, 85:4735 (1988) was digested with HindIII and SphI, and the 6-kb fragment containing CHS2 was ligated into the same sites of YEp352 (Hill et al., *Yeast*, 2:163 (1986). The resulting plasmid, pSS352, was digested with XbaI and religated, thereby deleting 1.3 kb of DNA, including the SalI site in the polylinker. This plasmid, pSS352ΔXba, and pJH-W1, a derivative of pUC18 that has a 1.4-kb fragment containing TRP1 inserted into the EcoRI site, were digested with BglII and SalI. The 8.7 fragment from pSS352ΔXba and the 0.9-kb TRP1 containing fragment from pJH-W1 were ligated together to give pCHS2W. After digestion with PvuII, the 3.9-kb fragment containing ch2::TRP1 was purified by electrophoresis onto DEAE-paper and used to transform (Ito et al *J. Bact.*, 153:163 (1983)) *S. cerevisiae* strain YPH274 (MAT a/α ura3-52/ura3-52 lys2-801/lys2-801 ade2-101/ade2-101 trp1-Δ1/trp1ΔIhis3-Δ200/his3-Δ200 leu2-Δl/leu2-Δl: Sikorski et al., *Genetics*, 122:19 (1989)) by transfornation. Trp+ transformants were sporulated, asci were dissected, and the spores were germinated on either SD medium (0.7% yeast nitrogen base without amino acids, 2% glucose, 2% agar) or YPG medium (2% Bacto peptone, 1% Bacto yeast extract, 3% glycerol, 2% agar) agar.

EXAMPLE 5

Detecting Chitin Synthase III Inhibitors with CHS2 Deficient Mutants

The minimum inhibitory concentrations (MIC) of two competitive inhibitors of chitin synthases, polyoxin D and nikkomycin Z, were determined against a wild-type strain, 58.5B, and three chitin synthase mutants 58.5A (chs1::URA3), 58.5C (chs2::TRP1), and 88.1A (csd2::LEU2). The constructions of chs1::URA3, chs2::TRP1, and csd2::LEU2 are described in Bulawa et al., *Cell*, 46:213 (1986), Example 2 and Bulawa, *Mol. Cell. Biol.*, 12:1764 (1992), respectively. The parent strain for all of the mutants is YPH274 (Sikorski et al., *Genetics*, 122:19 (1989). The complete genotypes of the strains are given below:

58.5A MATα ade2-101 his3-Δ200 leu2-Δ1 lys2-801 trp1-Δ1 ura3-52 Sup⁻(ssd1) chs1::URA3

58.5B MATa ade2-101 his3-Δ200 leu2-Δ1 lys2-801 trp1-Δ1 ura3-52 Sup⁻(ssd1)

58.5C MATa ade2-101 his3-Δ200 leu2-Δ1 lys2-801 trp1-Δ1 ura3-52 Sup⁻(ssd1) chs2::TRP1

88.1A MATα ade2-101 his3-Δ200 leu2-Δ1 lys2-801 trp1-Δ1 ura3-52 Sup⁻(ssd1) csd2::LEU2

As indicated above, Nikkomycin Z is an inhibitor of chitin synthase III. Polydoxin D is an inhibitor of chitin synthase I (Cabib, *Antimicrobiol Agent Chemother.*, 35:170 (1991).

Sterile water solutions of polyoxin D and nikkomycin Z (1 mg/ml) were serially diluted seven times (1:4, v/v with water). The sensitivity test was performed in a microtiter plate consisting of 96-wells in an array of 12 columns (labeled 1–12) and 8 rows (labeled A–G). Five $\mu$l of each dilution of polyoxin D was transferred in order of increasing concentration into the wells of columns 1, 4, 7 and 10. In a similar manner, nikkomycin Z was added to columns 3, 6, 9 and 12. As a control, water was added to columns 2, 5, 8 and 11. 100 $\mu$l of molten MAA was added to each of the 96-wells and allowed to solidify. Cell suspensions of each of the strains to be tested were prepared in sterile water ($A_{650}$ 0.02–0.05), and the wells were inoculated with 2.5 $\mu$l of cells as follows: 58.5B in columns 1–3, 58. 1A in columns 4–6, 58.5C in columns 7–9, and 88.1A in columns 10–12. After incubating at 30° C. for about 48 hours, MICs of the two drugs was determined for all four strains, as shown in the Table III. MIC is the lowest concentration of polyoxin D or nikkomycin Z which completely inhibits growth.

TABLE III

| Strain | Relevant Genotype | Minimal Inhibitor Concentration ($\mu$g/ml) | |
|---|---|---|---|
| | | Nikkomycin Z | Polyoxin D |
| 58.5B | Wild-type | >50 | >50 |
| 58.1A | chs1 | >50 | >50 |
| 58.5C | chs2 | 0.08–0.4 | >50 |
| 88.1A | csd2 | >50 | n.d |

As shown in the Table III, nikkomycin Z inhibits the growth of chs2 mutants, demonstrating that the assay detects inhibitors of chitin synthase III in intact cells. The related compound, polyoxin D, does not inhibit the growth of chs2 mutants. This indicates that the assay can identify chitin synthase III inhibitors and distinguish them from chitin synthase I inhibitors. Similar MIC's were obtained when ammonium sulfate (5 g/L) was substituted for allantoin. Much higher MIC's were obtained on medium containing yeast extract (5 g/L) and peptone (10 g/L) as the nitrogen source, probably due to inhibition of drug uptake (Mitani and Inoue, *J. Antibiot.* 21:492 (1968). Because all of the above strains are ssd1, conditions that do not support the growth of ssd1 csd2 double mutants cannot be used to demonstrate the nikkomycin hypersensitivity of the chs2 mutant 58.5C.

EXAMPLE 6

Determining Chitin Synthase III Inhibitors with ssd1 Mutants

SSD1 is polymorphic in laboratory strains of *S. cerevisiae* (Sutton et al., *Mol. Cell Biol*, 11:2133 (1991)). The different alleles of ssd1 do not, by themselves, produce any readily discernable phenotypes. However, some forms, designated ssd1, when combined with csd mutations, cause temperature-sensitive growth on media of low osmolarity (Bulawa, *Mol. Cell. Biol.*, 12, 12:1764 (1992) and Bulawa, *Ann. Rev. Microbiol.*, 47:505 (1993)). YPH274 was shown to be ssd1/ssd1 by demonstrating that in this strain, csd mutations cause temperature-sensitive growth on 0.5×YPD agar and the temperature-sensitivity is complemented by a plasmid containing SSD1. YPH274 was transformed with csd2-8::LEU2 as described in Bulawa, *Mol. Cell. Biol.*, 12, 12:1764 (1992). Several independent Leu⁺transformants were subjected to tetrad analysis; LEU2, ssd1, and csd2 were scored as the ability to grow on medium lacking leucine at 26° C., the inability to grow on 0.5×YPD agar at 36° C., and the ability to grow on YPDC agar at 260C, respectively. All three phenotypes, leucine prototrophy, temperature-sensitivity, and Calcofluor-resistance, co-segregrated. Leu⁺:Leu⁻, ts⁺:ts⁻, and Calcofluor-resistance:Calcofluor-sensitive all segregated 2:2. These results indicate that YPH274 is Sup⁻/Sup⁻. To show that Sup⁻is due to ssd1, several of the temperature-sensitive progeny were transformed with a plasmid, pCC75, consisting of a 7 kb DNA fragment containing SSD1 (Sutton et al., *Mol. Cell. Biol*. 11:2133 (1991) and Wilson et al., *Mol. Cell. Biol.* 11:3369 (1991)) cloned into YCp50 (ATCC37419). The transformants were able to grow on 0.5×YPD at 37° C. The ability of SSD1 to complement the temperature-sensitive phenotype indicates that this locus is defective in YPH274.

The MIC's of suspected inhibitors of chitin synthase III are determined against strains YPH274 strains 58.5B/YCp50 (URA3 ssd1) and 58.5B/pCC75 (URA3 SSD1). Strain 58.5B is a haploid derived from YPH274 by sporulation. Strain 58.5BJYCp50 was made by transforming 58.5B with YCp50, a low-copy plasmid containing URA3. Strain 58.5B/pCC75 was made by transforming 58.5B with pCC75, a low-copy plasmid containing URA3 and SSD1.

Suspected inhibitors of chitin synthase III are tested essentially as described in Example 5, except that strains 58.5B/YCp50 (URA3 ssd 1) and 58.5B/pCC75 (URA3 SSD1) are used, uracil is omitted from the MAA agar, and the incubation temperature is 37° C. Fermentation broths that preferentially inhibit the growth of 58.5B/YCp50 may contain inhibitors of chitin synthesis and will be subjected to further testing.

Equivalents

Those skilled in the art will know, or be able to ascertain using no more than routine experimentation, many equivalents to the specific embodiments of the invention described herein. These and all other equivalents are intended to be encompassed by the following claims.

What is claimed is:

1. A method of treating an individual with a fungal infection comprising the steps of:

a) culturing a mutant fungal strain, which contains a mutated gene whose presence in the mutant fungal strain together with inhibited chitin synthase III results in inhibited growth of the mutant fungal strain, in the presence of a compound to be assessed for its ability to inhibit fungal pathogenicity, under condition appropriate for growth of the mutant fungal strain;

b) culturing the corresponding wild type fungal strain in the presence of the compound to be assessed for its ability to inhibit fungal pathogenicity under the same conditions as used in step (a);

c) comparing the growth of the mutant fungal strain and the growth of the corresponding wild type fungal strain, wherein if growth of the mutant fungal strain is less than growth of the wild type fungal strain, the compound is identified as an inhibitor of fungal pathogenicity in the fungus in which chitin synthase III is necessary for pathogenicity;

d) confirming the therapeutic effectiveness of the inhibitor of fungal pathogenicity in an appropriate animal model; and e) administering to an individual a therapeutically effective amount of the inhibitor of fungal pathogenicity identified in step c.

2. The method of claim 1 wherein the inhibitor of fungal pathogenicity is co-administered with a therapeutically effective amount of a second anti-fungal agent.

3. A method of treating a plant fungal infection comprising the steps of:

(a) culturing a mutant fungal strain, which contains a mutated gene whose presence in the mutant fungal strain together with inhibited chitin synthase III results in inhibited growth of the mutant fungal strain, in the presence of a compound to be assessed for its ability to inhibit fungal pathogenicity, under condition appropriate for growth of the mutant fungal strain;

(b) culturing the corresponding wild type fungal strain in the presence of the compound to be assessed for its ability to inhibit fungal pathogenicity under the same conditions as used in step (a);

(c) comparing the growth of the mutant fungal strain and the growth of the corresponding wild type fungal strain, wherein if growth of the mutant fungal strain is less than growth of the wild type fungal strain, the compound is identified as an inhibitor of fungal pathogenicity in the fungus in which chitin synthase III is necessary for pathogenicity; and (d) contacting a plant with an effective amount of a compound identified in step (c).

4. The method of claim 3 wherein the inhibitor of fungal pathogenicity is co-administered with an effective amount of a second anti-fungal agent.

5. A method of treating an agricultural food product fungal contaminant comprising the steps of:

(a) culturing a mutant fungal strain, which contains a mutated gene whose presence in the mutant fungal strain together with inhibited chitin synthase III results in inhibited growth of the mutant fungal strain, in the presence of a compound to be assessed for its ability to inhibit the fungal contaminant, under condition appropriate for growth of the mutant fungal strain;

(b) culturing the corresponding wild type fungal strain in the presence of the compound to be assessed for its ability to inhibit the fungal contaminant under the same conditions as used in step (a);

(c) comparing the growth of the mutant fungal strain and the growth of the corresponding wild type fungal strain wherein if growth of the mutant fungal strain is less than growth of the wild type fungal strain, the compound is identified as an inhibitor of the fungal contaminant in which chitin synthase III is necessary for fungal contamination, and (d) contacting an agricultural food product with an effective amount of the compound identified in step (c).

6. The method of claim 5 wherein the inhibitor of the fungal contaminant is co-administered with an effective amount of a second anti-fungal agent.

7. A method of killing an insect comprising the steps of:

(a) culturing a mutant fungal strain, which contains a mutated gene whose presence in the mutant fungal strain together with inhibited chitin synthase III results in inhibited growth of the mutant fungal strain, in the presence of a compound to be assessed for insecticidal activity, under condition appropriate for growth of the mutant fungal strain;

(b) culturing the corresponding wild type fungal strain in the presence of the compound to be assessed for insecticidal activity under the same conditions as used in step (a);

(c) comparing the growth of the mutant fungal strain and the growth of the corresponding wild type fungal strain, wherein if growth of the mutant fungal strain is less than growth of the wild type fungal strain, the compound is identified as insecticidally active against the insect in which chitin synthase III is necessary for change; and (d) contacting an insect with an insecticidal amount of a compound identified by step(c).

* * * * *

UNITED STATES PATENT AND TRADEMARK OFFICE
CERTIFICATE OF CORRECTION

PATENT NO.   : 6,251,955 B1
DATED        : June 26, 2001
INVENTOR(S)  : Christine E. Bulawa It is certified that error appears in the above-identified patent and that said Letters Patent is hereby corrected as shown below:

Column 13, lines 65-67, through Column 14, lines 1-6 and lines 59-60,
Steps (a) and (b) should read:
-- a) culturing a mutant fungal strain, which contains a mutated gene whose presence in the mutant fungal strain together with inhibited chitin synthase III results in inhibited growth of the mutant fungal strain, in the presence of a compound to be assessed for its ability to inhibit fungal pathogenicity, under condition appropriate for growth of the mutant fungal strain;
   b) culturing the corresponding wild type fungal strain in the presence of the compound to be assessed for its ability to inhibit fungal pathogenicity under the same conditions as used in step (a); --

Signed and Sealed this

Eighteenth Day of June, 2002

Attest:

Attesting Officer

JAMES E. ROGAN
Director of the United States Patent and Trademark Office